United States Patent
Maeda et al.

(10) Patent No.: US 12,215,290 B2
(45) Date of Patent: Feb. 4, 2025

(54) NAPHTHYL PHENYL ETHER COMPOUND AND LUBRICANT COMPOSITION CONTAINING SAME

(71) Applicant: MORESCO CORPORATION, Kobe (JP)

(72) Inventors: Tatsuya Maeda, Hyogo (JP); Mayumi Hayashi, Hyogo (JP); Kohei Yamashita, Hyogo (JP); Masayuki Hata, Hyogo (JP)

(73) Assignee: MORESCO CORPORATION, Hyogo (JP)

( * ) Notice: Subject to any disclaimer, the term of this patent is extended or adjusted under 35 U.S.C. 154(b) by 0 days.

(21) Appl. No.: 18/276,156

(22) PCT Filed: Feb. 9, 2022

(86) PCT No.: PCT/JP2022/005002
§ 371 (c)(1),
(2) Date: Aug. 7, 2023

(87) PCT Pub. No.: WO2022/172934
PCT Pub. Date: Aug. 18, 2022

(65) Prior Publication Data
US 2024/0117265 A1   Apr. 11, 2024

(30) Foreign Application Priority Data
Feb. 12, 2021   (JP) ................. 2021-020367

(51) Int. Cl.
*C10M 105/18* (2006.01)
*C10N 20/04* (2006.01)

(52) U.S. Cl.
CPC .... *C10M 105/18* (2013.01); *C10M 2207/003* (2013.01); *C10M 2207/0406* (2013.01); *C10N 2020/04* (2013.01)

(58) Field of Classification Search
CPC .......... C10M 105/18; C10M 2207/003; C10M 2207/0406; C10N 2020/04
See application file for complete search history.

(56) References Cited

U.S. PATENT DOCUMENTS 4,664,829 A     5/1987  Arakawa et al.
4,892,680 A  *  1/1990  Ishida .................. C10M 105/38
                                                         508/505

FOREIGN PATENT DOCUMENTS

JP     62-59760      12/1987
JP     1-316340      12/1989

OTHER PUBLICATIONS

International Search Report issued Apr. 26, 2022 in International (PCT) Application No. PCT/JP2022/005002.
(Continued)

*Primary Examiner* — Taiwo Oladapo
(74) *Attorney, Agent, or Firm* — Wenderoth, Lind & Ponack, L.L.P.

(57) ABSTRACT

One aspect of the present invention relates to a naphthyl phenyl ether compound represented by formula (1):

[Chemical Formula 1]

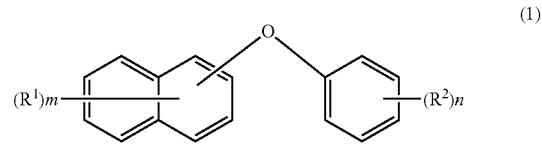

in the formula (1), $R^1$ and $R^2$ are the same or different and each represent a linear or branched hydrocarbon group
(Continued)

having 6 to 28 carbon atoms; m and n are each a real number of 0 or more and satisfy $1.0 \leq m+n \leq 3.0$.

3 Claims, 1 Drawing Sheet

(56) References Cited

OTHER PUBLICATIONS

Sethi, S.C. et al., "Preparation & Properties of Ethers of 3-Pentadecylphenol", Indian Journal of Technology, Jun. 1964, vol. 2, No. 6, pp. 206-208.

* cited by examiner

NAPHTHYL PHENYL ETHER COMPOUND AND LUBRICANT COMPOSITION CONTAINING SAME

TECHNICAL FIELD

The present invention relates to a naphthyl phenyl ether compound, and a lubricating oil composition and the like containing the same.

BACKGROUND ART

Lubricating oils and lubricating oil compositions are used for reducing friction and wear between moving parts or moving surfaces of various mechanical devices and the like.

In particular, lubricating oils, lubricating greases, and the like are being used under severer conditions such as high temperature, high speed, high load, and radiation, and lubricating oil agents having further improved heat resistance are required.

When the use condition becomes high in temperature and high in speed, lubricating oils, greases, and the like used for lubrication undergo temperature rise, thermal degradation, or oxidative degradation due to oil film breakage, and promotion of evaporation of lubricant base oils caused thereby leads to generation of sludge, breakage of a machine device, and life reduction.

For this reason, various lubricating oils and greases that can be used under high-temperature conditions have been studied, and in general, improvement under high-temperature conditions is largely caused by base oils contained most in the compositions of the lubricating oils and the greases.

Hitherto, a radiation-resistant lubricating oil containing 75 to 25% of a monoalkyl diphenyl ether or dialkyl diphenyl ether having 10 to 20 alkyl carbon atoms has been known (Patent Literature 1).

Furthermore, as a lubricating oil having oxidation stability, a naphthyl ether compound having an alkyl group having 1 to 20 carbon atoms, a phenyl group, a monoalkylphenyl group having 7 to 26 carbon atoms, and the like was also reported (Patent Literature 2).

The lubricating oil agent described in Patent Literature 1 is superior in heat resistance and radiation resistance, but currently, lubricating oil agents such as lubricating oil and lubricating grease have increasingly been used under severer conditions, and lubricating oil agents having further superior heat resistance are required. Further, in Patent Literature 2, the phenyl naphthyl ether compound actually used in Examples is butylphenyl naphthyl ether, and the studies by the present inventors revealed that this compound cannot afford sufficient heat resistance.

CITATION LIST

Patent Literatures

Patent Literature 1: JP-B-S62-59760
Patent Literature 2: JP-A-H1-316340

SUMMARY OF INVENTION

A task of the present invention is to solve the above problems. That is, an object of the present invention is to provide a compound which has further superior heat resistance and can be used as a lubricating oil that can be used under severer conditions.

As a result of intensive studies to solve the above task, the present inventors found that the above object is achieved by a naphthyl phenyl ether compound having the following configuration, and achieved the present invention by further conducting studies based on that finding.

That is, the naphthyl phenyl ether compound according to one aspect of the present invention is a compound represented by the following formula (1):

[Chemical Formula 1]

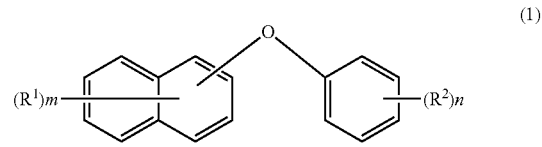

(1)

in the formula (1), $R^1$ and $R^2$ are the same or different and each represent a linear or branched hydrocarbon group having 6 to 28 carbon atoms; m and n are each a real number of 0 or more and satisfy $1.0 \leq m+n \leq 3.0$.

DESCRIPTION OF EMBODIMENTS

Figure 1:
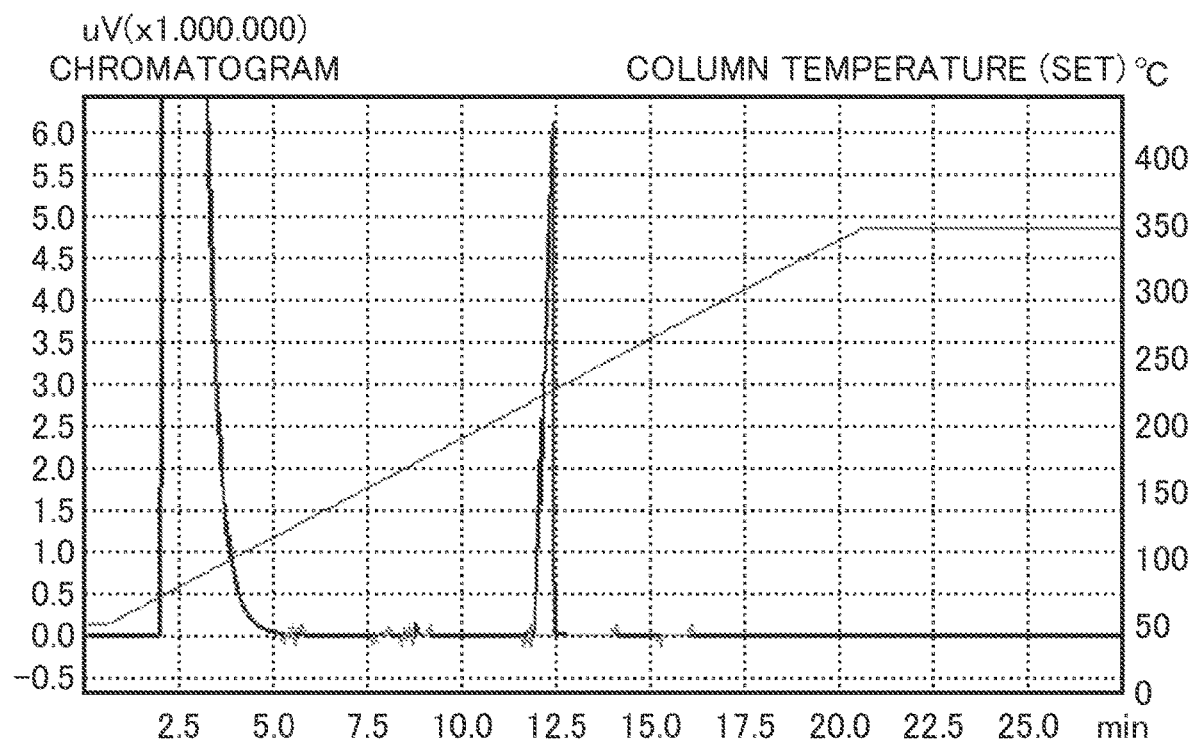
FIG. 1 shows a gas chromatography (GC) chart of the naphthyl phenyl ether synthesized in Example 1.

The naphthyl phenyl ether compound of the present invention is a compound represented by the following formula (1) as described above.

[Chemical Formula 2]

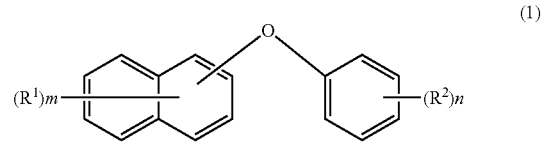

(1)

In the formula (1), $R^1$ and $R^2$ are the same or different and each represent a linear or branched hydrocarbon group having 6 to 28 carbon atoms. In addition, m and n are each a real number of 0 or more and satisfy $1.0 \leq m+n \leq 3.0$.

The naphthyl phenyl ether compound having such a configuration is very useful as a lubricating oil because the naphthyl phenyl ether compound has excellent heat resistance while maintaining low-temperature characteristics (pour point) and lubricity equivalent to those of conventional compounds like those described in the above-mentioned prior art documents. More specifically, since the naphthyl phenyl ether compound exhibits a small evaporation loss at a high temperature and has a long life at a high temperature, the naphthyl phenyl ether compound can be suitably used as a base oil of a lubricating oil for high temperature or a heat-resistant grease to be used at higher temperatures.

Therefore, according to the present invention, it is possible to provide a naphthyl phenyl ether compound that has further superior heat resistance and is used as a lubricating oil capable of being used under severer conditions.

Hereinafter, an embodiment of the present invention will be described in detail, but the present invention is not limited thereto.

The naphthyl phenyl ether compound of the present embodiment is a compound represented by the formula (1) provided above.

In the formula (1), $R^1$ and $R^2$ are the same or different and each represent a hydrocarbon group having 6 to 28 carbon atoms, and for example, when either m or n in the formula (1) is 0, either one of $R^1$ and $R^2$ may be a hydrogen atom. In other words, although either one of $R^1$ and $R^2$ may be a hydrogen atom, at least one of $R^1$ and $R^2$ is the hydrocarbon group defined above.

When the number of carbon atoms in the hydrocarbon group is less than 6, physical properties of naphthyl phenyl ether, which has no hydrocarbon groups, appear and the naphthyl phenyl ether compound is prone to solidify. In addition, its small molecular weight leads to a large evaporation amount. On the other hand, when the number of carbon atoms exceeds 28, the interaction between molecules becomes large, and the viscosity becomes excessively high. In addition, hydrocarbon groups are likely to aggregate, so that the pour point becomes excessively high. When $R^1$ and $R^2$ are each a hydrocarbon group having 6 to 28 carbon atoms, the naphthyl phenyl ether compound of the present embodiment has superior heat resistance, lubricity, and low-temperature fluidity together.

In the present embodiment, the structure of the hydrocarbon group having 6 to 28 carbon atoms is linear or branched. Specifically, examples of the linear hydrocarbon group include alkyl groups such as a hexyl group, an octyl group, a decyl group, a dodecyl group, a tetradecyl group, a hexadecyl group, an octadecyl group, an icosyl group, a docosyl group, a tetracosyl group, a hexacosyl group, and an octacosyl group; alkylene groups such as an octene group, a decene group, a hexadecene group, a dodecene group, an octadecene group, an icosene group, a dococene group, a techolacocene group, a hexacocene group, and an octacocene group; and a cyclohexyl group. Examples of the branched hydrocarbon group include a 1-methylundecyl group, a 1-ethyldecyl group, a 1-methyltridecyl group, a 1-ethyldodecyl group, a 1-methylpentadecyl group, a 1-ethyltetradodecyl group, a 1-methylheptadecyl group, a 1-ethyloctadecyl group, a 1-methylnonadecyl group, a 1-ethyloctadecyl group, a 2-ethylhexyl group, a 2-octyldodecyl group, a 2-decyltetradecyl group, a 2-dodecylhexadecyl group, a 1-butyl-1-methylpentyl group, a 1-butyl-1-methylheptyl group, a 1-methyl-1-pentyloctyl group, a 1-hexyl-1-methylnonyl group, a 1-heptyl-1-methyldecyl group, a 1-methyl-1-octylundecyl group, a 1-decyl-1-methyltridecyl group, a 1-dodecyl-1-methylpentadecyl group, a 2-octyldodecene group, a 2-decyltetradecene group, and a cyclohexyl group. The hydrocarbon group is preferably a saturated hydrocarbon group because of superior thermal stability. A plurality of kinds of the hydrocarbon group may be used at the same time. In this case, the number of carbon atoms of the hydrocarbon groups is represented by an average thereof.

Among these hydrocarbon groups, a hydrocarbon group having 12 to 24 carbon atoms is preferable from the viewpoint of affording further superior heat resistance, and preferred examples thereof include a 1-methylundecyl group, a 1-methyltridecyl group, a 1-methylpentadecyl group, a 1-methyl-1-octylundecyl group, a 1-decyl-1-methyltridecyl group, a 1-dodecyl-1-methylpentadecyl group, a hexadecyl group, a dodecyl group, a tetradecyl group, a 2-octyldodecyl group, a 2-decyltetradecyl group, and a 2-dodecylhexadecyl group.

In the formula (1), as long as m and n satisfy $1.0 \le m+n \le 3.0$, the hydrocarbon group as described above may be bonded to either a naphthyl group or a phenyl group and may be bonded to any position of the naphthyl group and the phenyl group. For example, when m+n is 1, either $R^1$ or $R^2$ may be a hydrogen atom.

In the compound of the formula (1), m and n are each a real number of 0 or more, and satisfy $1.0 \le m+n \le 3.0$. When m+n is less than 1.0, physical properties of naphthyl phenyl ether, which has no hydrocarbon groups, appear and the naphthyl phenyl ether compound is prone to solidify. In addition, a small molecular weight thereof makes it impossible to sufficiently control the evaporation amount. On the other hand, when m+n exceeds 3.0, this leads to a large interaction between molecules and affords an excessively high viscosity. In the present embodiment, m+n represents the number of substitution with linear or branched hydrocarbon groups (hereinafter, also simply referred to as the number of alkyl substitution).

The compound of the present embodiment may be, for example, a mixture of a compound with $0 \le m+n \le 2.0$ and a compound with $2.0 \le m+n \le 3.0$. In the case of a mixture of a plurality of compounds having different m+n values as described above, the value of m+n means the average value of m+n of the naphthyl phenyl ether compounds contained in the compound of the present embodiment.

In a preferred embodiment, the m+n is more desirably 1 or more and 2.5 or less.

In the present embodiment, the number of substitution with hydrocarbon groups can be measured by the method described in Examples described later.

Preferably, the mass average molecular weight of the naphthyl phenyl ether compound of the present embodiment is approximately 420 to 700. When the mass average molecular weight of the naphthyl phenyl ether compound is large, the compound tends to be superior in heat resistance, but the kinematic viscosity may be excessively high or the lubricity may be poor. On the other hand, when the mass average molecular weight is small, the kinematic viscosity decreases, but the heat resistance tends to be poor. When the mass average molecular weight is in the above range, there is an advantage that the kinematic viscosity and the pour point are not excessively high and the compound is superior in heat resistance.

The mass average molecular weight of the naphthyl phenyl ether compound in the present embodiment is a value measured using $^1$H-NMR as shown in Examples described later. Hereinafter, the mass average molecular weight is also simply referred to as "average molecular weight".

The method for producing the naphthyl phenyl ether compound as described above is not particularly limited, but for example, the naphthyl phenyl ether compound can be obtained by the following synthesis method.

First, 2-naphthol and N-methyl-2-pyrrolidone are mixed with potassium carbonate and copper iodide, followed by purging with nitrogen, and then bromobenzene is added dropwise thereto to afford naphthyl phenyl ether.

Next, the naphthyl phenyl ether compound of the present embodiment can be obtained, for example, by reacting the naphthyl phenyl ether with a linear or branched olefin or the like using aluminum chloride or the like as a catalyst.

The present invention also includes a lubricating oil composition containing the naphthyl phenyl ether compound described above.

In addition to the naphthyl phenyl ether compound, a mineral oil and a synthetic oil such as an α-olefin oligomer, a polyol ester, a diester, a polyalkylene glycol, silicone oil, a modified silicone oil, an alkyl diphenyl ether oil, a multiple alkylate cyclopentane oil, and a silahydrocarbon oil may be incorporated in the lubricating oil composition of the present embodiment, as necessary, for the purpose of further improving the performance thereof or in order to impart further performance as long as the effect of the present invention is not impaired. Furthermore, various additives such as an antioxidant, an extreme pressure agent, a friction modifier, a metal deactivator, an antifoaming agent, a thickener, and a coloring agent may, as necessary, be blended singly or in combination of two or more thereof.

As the additive, an antioxidant commonly used in a lubricating oil can be used without particular limitation, and examples of the antioxidant include phenol-based compounds, amine-based compounds, phosphorus-based compounds, and sulfur-based compounds.

Examples of the extreme pressure agent include phosphorus-based compounds and sulfur-based compounds.

Examples of the friction modifier include molybdenum-based compounds such as molybdenum dithiocarbamate, and fatty acid derivatives such as glycerin monostearate.

Examples of the metal deactivator include benzotriazole-based, tolyltriazole-based, thiadiazole-based, and imidazole-based compounds.

Examples of the antifoaming agent include polyacrylates and styrene ester polymers.

Examples of the thickener include metal soaps (for example, lithium soap), silica, expanded graphite, polyurea, and clays (for example, hectorite or bentonite).

In the lubricating oil composition of the present embodiment, when the naphthyl phenyl ether compound is contained as a base oil, the content thereof is preferably approximately 50 to 100 mass % with respect to the entire (total mass) of the lubricating oil composition from the viewpoint of ensuring heat resistance. In this case, the content of the additives in the lubricating oil composition is preferably approximately 50 to 0 mass %.

Furthermore, it is also possible to use the naphthyl phenyl ether compound as an additive of a lubricating oil composition, and in this case, the content of the naphthyl phenyl ether compound is preferably approximately 1 to 49 mass % with respect to the entire (total mass) of the lubricating oil composition.

The present invention also includes a lubricating oil for high temperature and a heat-resistant grease each containing the naphthyl phenyl ether compound described above.

The lubricating oil composition, the lubricating oil for high temperature, and the heat-resistant grease described above are suitably used as a lubricant for bearings, a lubricant for impregnated bearings, a grease base oil, a freezer oil, a plasticizer, and the like. In particular, they can be suitably used as various lubricating oils to be used under high-temperature conditions, such as a bearing oil, a fluid bearing oil, an oil-containing bearing oil, a grease base oil, an oil-containing plastic oil, a gear oil, a jet engine oil, a heat insulating engine oil, a gas turbine oil, an automatic transmission oil, a vacuum pump oil, and a hydraulic operating fluid.

In addition, since the naphthyl phenyl ether compound described above is also superior in radiation resistance, it is conceivable that the naphthyl phenyl ether compound can be suitably used as a radiation-resistant lubricating oil or a radiation-resistant grease.

Although the present description discloses the techniques of various aspects as described above, the main technology among them is summarized below.

The naphthyl phenyl ether compound according to one aspect of the present invention is a compound represented by the following formula (1):

[Chemical Formula 3]

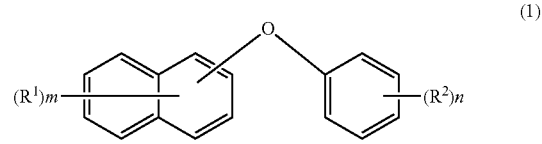

(1)

in the formula (1), $R^1$ and $R^2$ are the same or different and each represent a linear or branched hydrocarbon group having 6 to 28 carbon atoms; m and n are each a real number of 0 or more and satisfy $1.0 \leq m+n \leq 3.0$.

With such a configuration, it is possible to provide a compound having heat resistance superior to conventional lubricating oils.

The lubricating oil composition according to another aspect of the present invention is characterized by containing the naphthyl phenyl ether compound described above.

The lubricating oil for high temperature and the radiation-resistant lubricating oil according to still another aspect of the present invention are characterized by containing the naphthyl phenyl ether compound described above.

The heat-resistant grease and the radiation-resistant grease according to still another aspect of the present invention are characterized by containing the naphthyl phenyl ether compound described above.

The lubricating oil composition, the lubricating oil for high temperature, and the heat-resistant grease according to the present invention have excellent heat resistance, and thus are suitable for use under severe conditions (particularly, at high temperatures).

EXAMPLES

Hereinafter, examples of the present invention will be described, but the present invention is not limited thereto.

Synthesis of Compounds

Example 1: Compound 1

A four-necked flask equipped with a stirrer, a thermometer, a dropping funnel, and a cooling tube and having a capacity of 5 L was charged with 504 g (3.50 mol) of 2-naphthol, 961 g (6.95 mol) of potassium carbonate, 135 g (0.71 mol) of copper iodide, and 1500 g of N-methyl-2-pyrrolidone (hereinafter, referred to as NMP) and purged with nitrogen, and then the temperature of the reaction system was heated to 175° C. When the temperature reached 120° C., dropwise addition of 1120 g (7.13 mol) of bromobenzene was started. After completion of the dropwise addition, the mixture was stirred at 175° C. for 6 hours. After completion of the reaction, the mixture was allowed to spontaneously cool until the temperature reached 90° C. Then, 60 g of KYOWAAD 1000s (alkaline adsorbent; manufactured by Kyowa Chemical Industry Co., Ltd.) was added and the resulting mixture was stirred for 30 minutes. Subsequently, 40 g of activated clay was added, and the mixture was stirred at 90° C. for 30 minutes, and then a solid component was removed by filtration under reduced pressure. The filter cake was stirred in NMP and vacuum filtration was repeated three times. The obtained filtrate was distilled under reduced pressure at 80 Pa at 165° C. to 170° C. Thus, 2-naphthyl phenyl ether (2-naphthyl phenyl oxide: 2-NPO), which was solid at normal temperature, was obtained as a fraction. To the resulting mixture was added 5 weight % of active clay, and the resulting mixture was stirred at 90° C. for 30 minutes, and contaminating grease and the like were removed by reduced pressure filtration. A gas chromatography (GC) chart of naphthyl phenyl ether is shown in FIG. 1 (the measurement conditions will be described later.). The purity was 98.7%. The naphthyl phenyl ether synthesized here was used also as a reaction material in Examples 2 to 6 described later.

Next, a 500 mL four-necked flask equipped with a stirrer, a dropping funnel, and a thermometer was charged with 200 g (0.91 mol) of the naphthyl phenyl ether obtained above and 2.85 g (0.021 mol) of anhydrous aluminum chloride, and the mixture was heated to 90° C. to dissolve the anhydrous aluminum chloride. Then, 102 g (0.45 mol) of 1-hexadecene was added dropwise over 2 hours while maintaining the temperature of the reaction system at 110° C., and a substitution reaction was performed. After completion of the dropwise addition, stirring was continued at 110° C. for 5 hours, and then the mixture was allowed to spontaneously cool until the temperature reached 90° C. Then, KYO-WAAD 1000s in an amount 5.5 times the amount of anhydrous aluminum chloride was charged, and the mixture was stirred for 30 minutes. Subsequently, active clay in an amount 3.65 times the amount of anhydrous aluminum chloride was charged, the mixture was stirred at 90° C. for 30 minutes, and then anhydrous aluminum chloride and other acidic substances produced as by-products were removed by filtration under reduced pressure. The filtrate obtained here was distilled under reduced pressure at 260° C. at 80 Pa to remove unreacted raw materials and the like, thereby affording alkyl-substituted naphthyl phenyl ether (Compound 1: alkyl (C16)-2-phenoxynaphthalene (C16-2-NPO)) mainly composed of monoalkyl-substituted bodies. To the resulting mixture was added 5 weight % of active clay, and the resulting mixture was stirred at 90° C. for 30 minutes, and contaminating grease and the like were removed by reduced pressure filtration. The evaluation was performed for Compound 1 from which grease and the like had been removed. Hereinafter, in Examples 2 to 7 and Comparative Examples 1 to 3, grease and the like were removed, followed by the evaluation, in the same manner.

Example 2: Compound 2

An alkyl-substituted naphthyl phenyl ether (Compound 2: dialkyl (C16)-2-phenoxynaphthalene (diC16-2-NPO)) mainly composed of dialkyl-substituted bodies was obtained under the same conditions as in Example 1 except that a four-necked flask having a capacity of 500 mL was used for the reaction, 130 g (0.59 mol) of the naphthyl phenyl ether obtained in Example 1, 1.11 g (0.0083 mol) of anhydrous aluminum chloride, and 39.7 g (0.18 mol) of 1-hexadecene were used, and unreacted raw materials, monoalkyl-substituted bodies and the like were removed by distillation under reduced pressure at 300° C. at 80 Pa.

Example 3: Compound 3

An alkyl-substituted naphthyl phenyl ether (Compound 3: alkyl (C12)-2-phenoxynaphthalene (C12-2-NPO)) mainly composed of monoalkyl-substituted bodies was obtained under the same conditions as in Example 1 except that a four-necked flask having a capacity of 500 mL was used for the reaction, 100 g (0.45 mol) of the naphthyl phenyl ether obtained in Example 1, 1.07 g (0.0080 mol) of anhydrous aluminum chloride, and 38.2 g (0.23 mol) of 1-dodecene were used, and monoalkyl-substituted bodies were obtained as a fraction through distillation under reduced pressure at 260° C. to 300° C. at 80 Pa.

Example 4: Compound 4

An alkyl-substituted naphthyl phenyl ether (Compound 4: dialkyl (C12)-2-phenoxynaphthalene (diC12-2-NPO)) mainly composed of dialkyl-substituted bodies was obtained under the same conditions as in Example 1 except that a four-necked flask having a capacity of 500 mL was used for the reaction, 100 g (0.45 mol) of the naphthyl phenyl ether obtained in Example 1, 1.93 g (0.014 mol) of anhydrous aluminum chloride, and 68.77 g (0.41 mol) of 1-dodecene were used, and distillation under reduced pressure was performed at 300° C. at 80 Pa.

Example 5: Compound 5

An alkyl-substituted naphthyl phenyl ether (Compound 5: branched alkyl (C20)-2-phenoxynaphthalene (bC20-2-NPO)) mainly composed of monoalkyl-substituted bodies was obtained under the same conditions as in Example 1 except that a four-necked flask having a capacity of 500 mL was used for the reaction, and 135 g (0.61 mol) of the naphthyl phenyl ether obtained in Example 1, 2.40 g (0.018 mol) of anhydrous aluminum chloride, and 85.8 g (0.31 mol) of 2-octyl-1-dodecene were used.

Example 6: Compound 6

An alkyl-substituted naphthyl phenyl ether (Compound 6: branched alkyl (C24)-2-phenoxynaphthalene (bC24-2-NPO)) mainly composed of monoalkyl-substituted bodies was obtained under the same conditions as in Example 1 except that a four-necked flask having a capacity of 100 mL was used for the reaction, and 33 g (0.15 mol) of the naphthyl phenyl ether obtained in Example 1, 0.71 g (0.0053 mol) of anhydrous aluminum chloride, and 85.8 g (0.31 mol) of 2-decyl-1-tetradecene were used.

Example 7: Compound 10

A four-necked flask equipped with a stirrer, a thermometer, a dropping funnel, and a cooling tube and having a capacity of 2 L was charged with 250 g (1.73 mol) of 1-naphthol, 479 g (3.47 mol) of potassium carbonate, 66 g (0.35 mol) of copper iodide, and 380 g of NMP and purged with nitrogen, and then the temperature of the reaction system was heated to 175° C. When the temperature reached 120° C., dropwise addition of 545 g (3.47 mol) of bromobenzene was started. After completion of the dropwise addition, the mixture was stirred at 175° C. for 6 hours. After completion of the reaction, the mixture was allowed to spontaneously cool to 90° C., 30 g of KYOWAAD 1000s was added, and the mixture was stirred for 30 minutes. Subsequently, 20 g of activated clay was added, and the mixture was stirred at 90° C. for 30 minutes, and then a solid component was removed by filtration under reduced pressure. The filter cake was stirred in NMP and vacuum filtration was repeated three times. The obtained filtrate was distilled under reduced pressure at 80 Pa from 165° C. to 170° C. Thus, 1-naphthyl phenyl ether (1-naphthyl phenyl oxide: 1-NPO) was obtained as a fraction. To the resulting mixture was added 5 weight % of active clay, and the resulting mixture was stirred at 90° C. for 30 minutes, and contaminating grease and the like were removed by reduced pressure filtration. The purity was 99.0%.

Next, a 500 mL four-necked flask equipped with a stirrer, a dropping funnel, and a thermometer was charged with 110 g (0.50 mol) of the 1-naphthyl phenyl ether obtained above and 1.57 g (0.012 mol) of anhydrous aluminum chloride, and the mixture was heated to 90° C. to dissolve the anhydrous aluminum chloride. Then, 56 g (0.25 mol) of 1-hexadecene was added dropwise over 1 hour while maintaining the temperature of the reaction system at 110° C., and a substitution reaction was performed. After completion of the dropwise addition, stirring was continued at 110° C. for 5 hours, and then the mixture was allowed to spontaneously cool until the temperature reached 90° C. Then, KYOWAAD 1000s in an amount 5.5 times the amount of anhydrous aluminum chloride was charged, and the mixture was stirred for 30 minutes. Subsequently, active clay in an amount 3.65 times the amount of anhydrous aluminum chloride was charged, the mixture was stirred at 90° C. for 30 minutes, and then anhydrous aluminum chloride and other acidic substances produced as by-products were removed by filtration under reduced pressure. The filtrate obtained here was distilled under reduced pressure at 260° C. at 80 Pa to remove unreacted raw materials and the like, thereby affording alkyl-substituted naphthyl phenyl ether (Compound 10: alkyl (C16)-1-phenoxynaphthalene (C16-1-NPO)) mainly composed of monoalkyl-substituted bodies. To the resulting mixture was added 5 weight % of active clay, and the resulting mixture was stirred at 90° C. for 30 minutes, and contaminating grease and the like were removed by reduced pressure filtration.

Comparative Example 1: Compound 7

A 500 mL four-necked flask equipped with a stirrer, a dropping funnel, and a thermometer was charged with 200 g (1.18 mol) of diphenyl ether and 1.00 g (0.0075 mol) of anhydrous aluminum chloride were put, and the mixture was heated to 90° C. to dissolve the anhydrous aluminum chloride. Thereafter, while the temperature of the reaction system was maintained at 100° C., 186 g (0.83 mol) of 1-hexadecene was added dropwise over 2 hours and a substitution reaction was performed. After completion of the dropwise addition, stirring was continued at 100° C. for 1 hour, and then the mixture was allowed to spontaneously cool until the temperature reached 90° C. Then, KYOWAAD 1000s in an amount 5.5 times the amount of anhydrous aluminum chloride was charged, and the mixture was stirred for 30 minutes. Subsequently, active clay in an amount 3.65 times the amount of anhydrous aluminum chloride was charged, the mixture was stirred at 90° C. for 30 minutes, and then anhydrous aluminum chloride and other acidic substances produced as by-products were removed by filtration under reduced pressure. The filtrate (reaction filtrate A) obtained here was distilled under reduced pressure at 250° C. to 260° C. at 80 Pa, affording a monoalkyl-substituted diphenyl ether (Compound 7: alkyl (C16) diphenyl ether (C16-DPO)) as a fraction. To the resulting mixture was added 5 weight % of active clay, and the resulting mixture was stirred at 90° C. for 30 minutes, and contaminating grease and the like were removed by reduced pressure filtration.

Comparative Example 2: Compound 8

The reaction filtrate A obtained in Comparative Example 1 was distilled under reduced pressure at 290° C. at 80 Pa to remove unreacted raw materials, monoalkyl-substituted bodies and the like, thereby affording alkyl-substituted diphenyl ether (Compound 8: dialkyl (C16) diphenyl ether (diC16-DPO)) mainly composed of dialkyl-substituted bodies.

Comparative Example 3: Compound 9

A four-necked flask equipped with a stirrer, a thermometer, a dropping funnel, and a cooling tube and having a capacity of 5 L was charged with 100 g (0.67 mol) of 4-sec-butylphenyl, 275 g (1.33 mol) of 1-bromonaphthalene, 138 g (1.33 mol) of potassium carbonate, 25 g (0.13 mol) of copper iodide, and 350 g of N-methyl-2-pyrrolidone (hereinafter, referred to as NMP) and purged with nitrogen. Thereafter, the mixture was stirred at 175° C. for 12 hours. After completion of the reaction, the mixture was allowed to spontaneously cool to 90° C., 20 g of KYOWAAD 1000s was added, and the mixture was stirred for 30 minutes. Subsequently, 15 g of activated clay was added, and the mixture was stirred at 90° C. for 30 minutes, and then a solid component was removed by filtration under reduced pressure. The filter cake was stirred in NMP and vacuum filtration was repeated three times. The obtained filtrate was distilled under reduced pressure at 80 Pa at 190° C. to 220° C. Thus, 4-sec-butylphenyl-1-naphthyl ether (Compound 9) was obtained as a fraction. To the resulting mixture was added 5 weight % of active clay, and the resulting mixture was stirred at 90° C. for 30 minutes, and contaminating grease and the like were removed by reduced pressure filtration.

[$^1$H-NMR measurement conditions and conditions for calculation of number of substitution with hydrocarbon groups] $^1$H-NMR was measured using a nuclear magnetic resonance apparatus JNM-ECX400 manufactured by JEOL Ltd. The measurement was conducted at a temperature of 80° C. with no use of solvents and standard substances.

The chemical shift was determined by performing measurement of the same compound using deuterated chloroform as a solvent and TMS as a standard substance and comparing the results. This is because peaks of deuterated chloroform and a benzene ring overlap each other, and an accurate integral value cannot be obtained.

Compounds 1 to 10 obtained were analyzed using $^1$H-NMR under the above conditions, and the mass average molecular weight of each compound was determined.

The number of substitution with hydrocarbon groups in Compounds 1 to 10 was determined through analyzing a $^1$H-NMR spectrum for each compound. Specifically, a calculation method will be described using the $^1$H-NMR spectrum of a model compound shown in FIG. 2.

Figure 2:
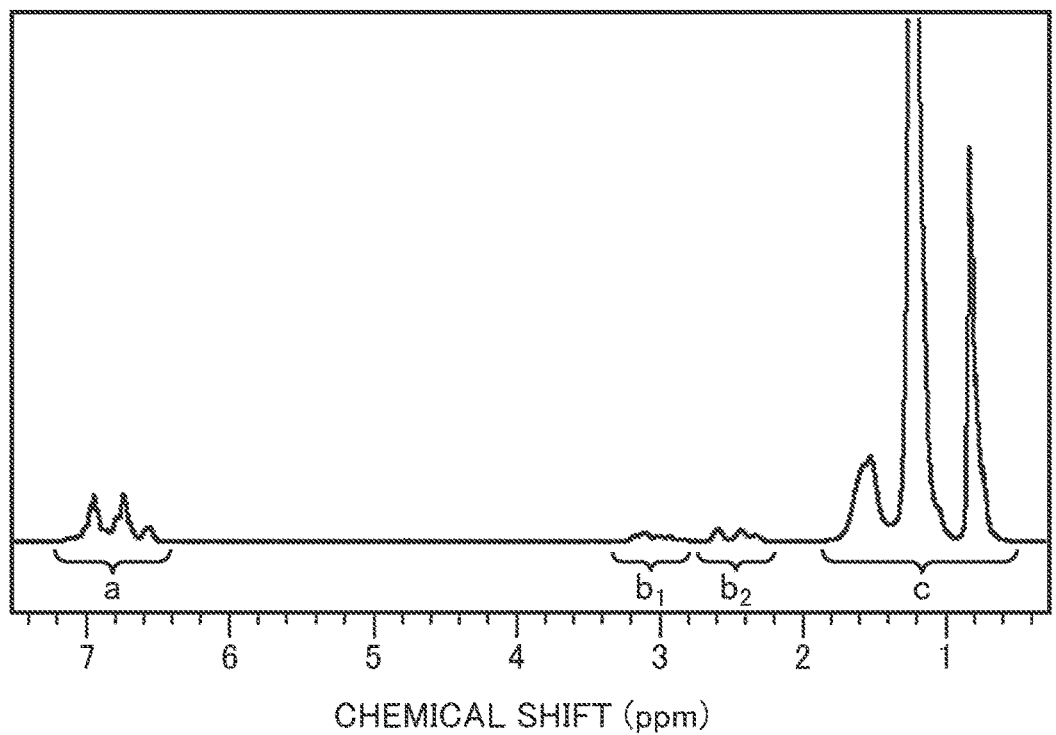
FIG. 2 shows a $^1$H-NMR spectrum of a model compound for determining the number of substitution with hydrocarbon groups.

In FIG. 2, a (chemical shift: 6.5 to 7.3) represents a peak of hydrogen of an aromatic ring. $b_1$ (chemical shift: 2.8 to 3.3) and $b_2$ (chemical shift: 2.2 to 2.7) represent peaks of hydrogen at the benzyl position. c (chemical shift: 0.5 to 1.9) represents a peak of hydrogen of a hydrocarbon group.

Based on the integrated values (ratios) of the peaks a, $b_1$, $b_2$, and c, the number of substitution with hydrocarbon groups is calculated by the following formula:

Number of substitution with hydrocarbon groups
$(m+n)$=(number of hydrogen atoms of aromatic ring)$\times(b_1+b_2+c)$/[(average number of hydrogen atoms of hydrocarbon group)$\times a+b_1+b_2+c$]

[Fluidity]

The pour point (° C.) of Compounds 1 to 10 was measured according to JIS K 2269 (1987). In this test, a pour point of −20° C. or lower is determined to be acceptable.

[Viscosity Properties]

The kinematic viscosity (mm²/s) at 40° C. was measured and calculated in accordance with JIS K 2283 (2000).

The above results are summarized in Tables 1 and 2.

TABLE 1

|  | Example 1 Compound 1 | Example 2 Compound 2 | Example 3 Compound 3 | Example 4 Compound 4 | Example 5 Compound 5 | Example 6 Compound 6 | Example 7 Compound 10 |
|---|---|---|---|---|---|---|---|
| Average number of substitution with hydrocarbon groups (n + m) | 1.27 | 1.93 | 1.23 | 2.42 | 1.25 | 1.30 | 1.20 |
| Number of carbon atoms of hydrocarbon group | 16 | 16 | 12 | 12 | 20 | 24 | 16 |
| Average molecular weight | 505 | 653 | 427 | 628 | 571 | 661 | 627 |
| [TG] Evaporation amount (%) at 250° C. for 30 minutes | 11.22 | 4.35 | 26.30 | 5.20 | 7.22 | 6.73 | 17.13 |
| 200° C. Thin film life (hours) | 46 | 34 | 32 | 40 | 52 | 48 | 36 |
| Average COF at 100N | 0.144 | 0.106 | 0.134 | 0.107 | 0.141 | 0.134 | 0.139 |
| Pour point (° C.) | −35 | −20 | −37.5 | −30 | −37.5 | −40 | −35 |
| 40° C. Kinematic viscosity (mm²/s) | 118.4 | 271.0 | 97.2 | 310.0 | 192.0 | 218.8 | 141.5 |

<Purity Measurement>
[Gas Chromatography (GC) Measurement Conditions]

Gas chromatography was measured using GC-2010 Plus manufactured by Shimadzu Corporation. The column used was Ultra ALLOY+-17, and nitrogen gas was used as a carrier gas. The measurement temperature conditions were as follows: the temperature was held at 50° C. for 2 minutes, then raised 25° C. per minute up to 100° C., and from 100° C., raised 15° C. per minute up to 350° C., and held at 350° C. for 15 minutes.

<Evaluation Test>
[Measurement of Evaporation Amount by TG Method]

The evaporation amount determined by a TG method was measured using ST7200RV manufactured by Hitachi High-Technologies Corporation. Using air (200 ml/min) as a carrier gas and an aluminum deep pan as a sample container, an evaporation amount (%) of each compound at the time of holding 5 mg of a sample at a temperature of 250° C. for 30 minutes was measured.

In this test, the evaluation criteria is that a compound satisfying an evaporation amount after 30 minutes of 27% or less is determined to be acceptable.

[Thin Film Heating Test]

0.5 g of each of the Compounds 1 to 10 was weighed in a 50 (D concave dish made of material S45C. This was left at rest in a thermostatic chamber at 200° C., taken out from the thermostatic chamber every 2 hours, subjected to weight measurement, and checked for fluidity at the time of having been returned to room temperature. The time at which the fluidity at room temperature was lost was defined as a thin film life. In this test, a thin film life of 25 hours or more is determined to be acceptable.

[Lubricity Test (SRV)]

Lubricity was measured using SRV-5 manufactured by Optimol Instruments Prüftechnik GmbH. A ½ inch SUJ2 ball was used as an upper specimen, and a SK-5 plate was used as a lower specimen. After a running-in operation at a temperature of 40° C., a load of 50 N, and a speed of 40 mm/s for 50 seconds, this test at a temperature of 40° C., a load of 100 N, and a speed of 40 mm/s for 600 seconds was performed to measure a coefficient of friction (COF), and an average COF at 100 N was determined. In this test, an average COF of 0.150 or less is determined to be acceptable.

TABLE 2

|  | Comparative Example 1 Compound 7 | Comparative Example 2 Compound 8 | Comparative Example 3 Compound 9 |
|---|---|---|---|
| Average number of substitution with hydrocarbon groups (n + m) | 1.05 | 2.22 | 1.00 |
| Number of carbon atoms of hydrocarbon group | 16 | 16 | 4 |
| Average molecular weight | 406 | 668 | 226 |
| [TG] Evaporation amount (%) at 250° C. for 30 minutes | 81.56 | 27.40 | 78.76 |
| 200° C. Thin film life (hours) | 4 | 14 | 2 |
| Average COF at 100N | 0.162 | 0.187 | 0.197 |
| Pour point (° C.) | −35 | 0 | −25 |
| 40° C. Kinematic viscosity (mm²/s) | 21.3 | 87.7 | 38.0 |

Discussion

The results in Table 1 showed that the naphthyl phenyl ether compounds 1 to 6 and the compound 10 of Examples related to the present invention satisfied all the acceptance criteria for both the evaporation amount and the thin film life described above. That is, it was found that since the evaporation loss at a high temperature was small and the life at a high temperature is long, those compounds were excellent in heat resistance. It is known that the evaporation amount normally increases as the molecular weight of the compound decreases. However, the evaporation amount was controlled with the compounds of the present invention in Examples 1, 2 and 7 as compared with Comparative Example 2 even with the same number of carbon atoms of the hydrocarbon group. In Examples 2, 4, 6, and 7, the evaporation amount was controlled as compared with Comparative Examples 2 even with an equivalent molecular weight. Comparison between Example 3 and Comparative Example 2 which are equivalent in kinematic viscosity revealed that the case with the structure of the present invention is superior in coefficient of friction. As a result of comparison of Examples 1 to 7 with Comparative Example 3, Example 1 to 7 exhibited better properties due to the difference in the number of carbon atoms of the hydrocarbon group ($R^1$ and/or $R^2$) although in the same naphthyl ether category. Furthermore, it was also confirmed that the compound of the present invention has performance comparable to that of compounds conventionally used as a lubricant also in low-temperature fluidity and lubricity. In Examples, the kinematic viscosity at 40° C. was higher than that in Comparative Examples, but the products could be used as a lubricant. Therefore, it was confirmed that when the hydrocarbon group of a naphthyl phenyl ether has 6 to 28 carbon atoms and the number of substitution with hydrocarbon groups is $1.0 \leq m+n \leq 3.0$, the naphthyl phenyl ether has heat resistance, low-temperature fluidity, and lubricity together.

On the other hand, according to the results in Table 2, the conventionally used diphenyl ether compounds of Comparative Examples 1 and 2 and the butylphenyl naphthyl ether of Comparative Example 3 were large in the evaporation amount and short in thin film life, and could not obtain heat resistance as much as the compound of the present invention. In all Examples and Comparative Examples 1 and 2, fluidity could be confirmed again when the ambient temperature was raised to a temperature equal to or higher than the pour point after the pour point measurement, but in Comparative Example 3, even when the ambient temperature was returned to room temperature, the sample remained solid.

It is considered that since NPO is solid at normal temperature and, in Comparative Example 3 in which $R^2$ has 4 carbon atoms and $m+n=1$, the hydrocarbon group is short, the physical properties of NPO greatly acted and the product had a property of easily solidifying. In addition, it is considered that when the number of carbon atoms in the hydrocarbon group exceeds 28, the interaction between molecules increases, so that the viscosity and the pour point become excessively high.

This application is based on Japanese Patent Application No. 2021-020367 filed on Feb. 12, 2021, the contents of which are included in the present application.

In order to embody the present invention, the present invention has been appropriately and sufficiently described through the embodiments with reference to the specific examples in the above, but it should be recognized that those skilled in the art can easily modify and/or improve the above-described embodiments. Therefore, as long as modifications or improvements carried out by a person skilled in the art do not depart from the scope of the claims described in the patent claims of the present invention, these modifications or improvements are interpreted as being encompassed by the scope of the claims.

INDUSTRIAL APPLICABILITY

Since the naphthyl phenyl ether compound of the present invention is excellent in heat resistance, it can be suitably used as a lubricating oil for high temperature, a heat-resistant grease, and the like, and has wide industrial applicability.

The invention claimed is:

1. A lubricating oil composition comprising a naphthyl phenyl ether compound represented by the following formula (1):

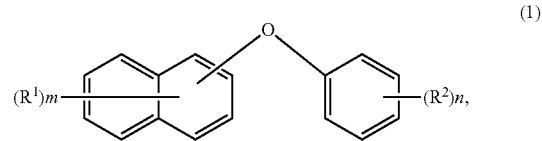

wherein in formula (1), $R^1$ and $R^2$ are the same or different and each represent a linear or branched hydrocarbon group having 6 to 28 carbon atoms; m and n are each a real number of 0 or more and satisfy $1.2 \leq m+n \leq 3.0$.

2. The lubricating oil composition according to claim 1, wherein $R^1$ and $R^2$ of the naphthyl phenyl ether compound are the same or different and each represent a linear or branched hydrocarbon group having 12 to 28 carbon atoms.

3. The lubricating oil composition according to claim 1, wherein the naphthyl phenyl ether compound has a mass average molecular weight of 420 to 700.

* * * * *